United States Patent [19]
Johnson

[11] Patent Number: 5,702,374
[45] Date of Patent: Dec. 30, 1997

[54] MALE LUER CONNECTOR ASSEMBLY

[75] Inventor: Robert H. Johnson, Fountain Green, Utah

[73] Assignee: Abbott Laboratories, Abbott Park, Ill.

[21] Appl. No.: 557,214

[22] Filed: Nov. 14, 1995

[51] Int. Cl.⁶ ............................................. A61M 25/00
[52] U.S. Cl. .......................... 604/283; 604/905; 285/330; 285/332; 285/387; 128/912
[58] Field of Search ............................ 604/283, 905; 128/DIG. 26, 897, 898, 912; 285/387, 388, 330, 332, 92

[56] References Cited

U.S. PATENT DOCUMENTS

| | | | |
|---|---|---|---|
| 4,266,815 | 5/1981 | Cross | 285/330 |
| 4,452,473 | 6/1984 | Ruschke | 604/283 |
| 4,735,441 | 4/1988 | Stephens | 285/332 |
| 5,047,021 | 9/1991 | Utterberg | 285/332 |
| 5,549,583 | 8/1996 | Sanford et al. | 604/905 |

*Primary Examiner*—Michael Powell Buiz
*Assistant Examiner*—Ronald K. Stright, Jr.
*Attorney, Agent, or Firm*—Neal D. Marcus; Ronald M. Anderson

[57] ABSTRACT

An improved male luer connector assembly including a central elongated male luer connector tapering from a distal end to a locking collar disposed approximately at the midpoint of the connector. A recessed section is disposed between the first collar and a second collar. Locking teeth are disposed on a proximal face of the locking collar in spaced relation. A threaded lock nut is mountable on the male luer connector. An inner peripheral end wall of the lock nut surrounds the male luer connector and carries a ratchet at an inner end face thereof. In the connection of the male luer connector assembly to a complementary female threaded luer connector, the engaging teeth on the proximal face of the locking collar are drawn into engagement with the ratchet on the inner face of the lock nut to ensure and maintain a locking fluid-tight connection between said male luer connector assembly and the female luer connector.

5 Claims, 4 Drawing Sheets

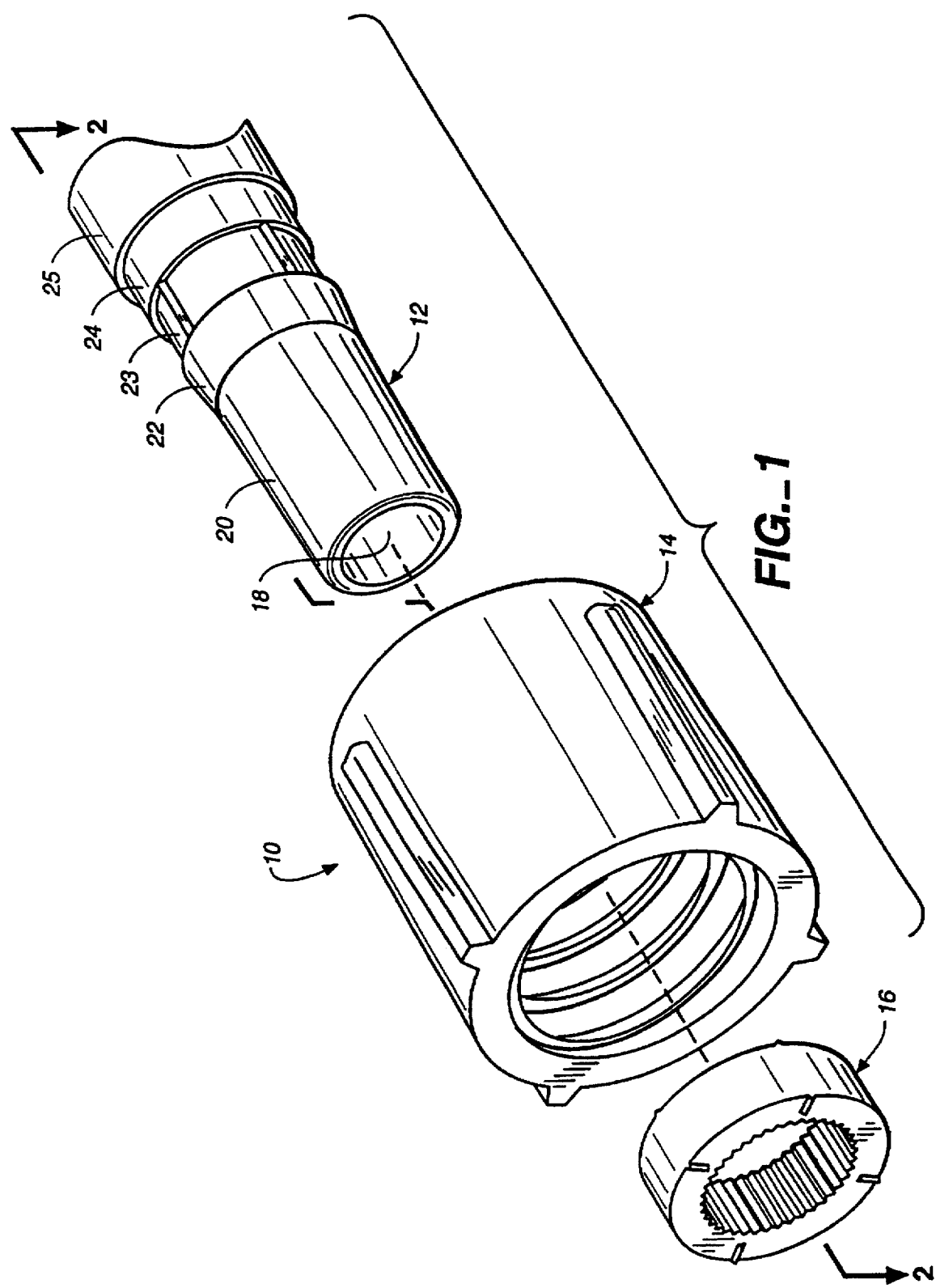

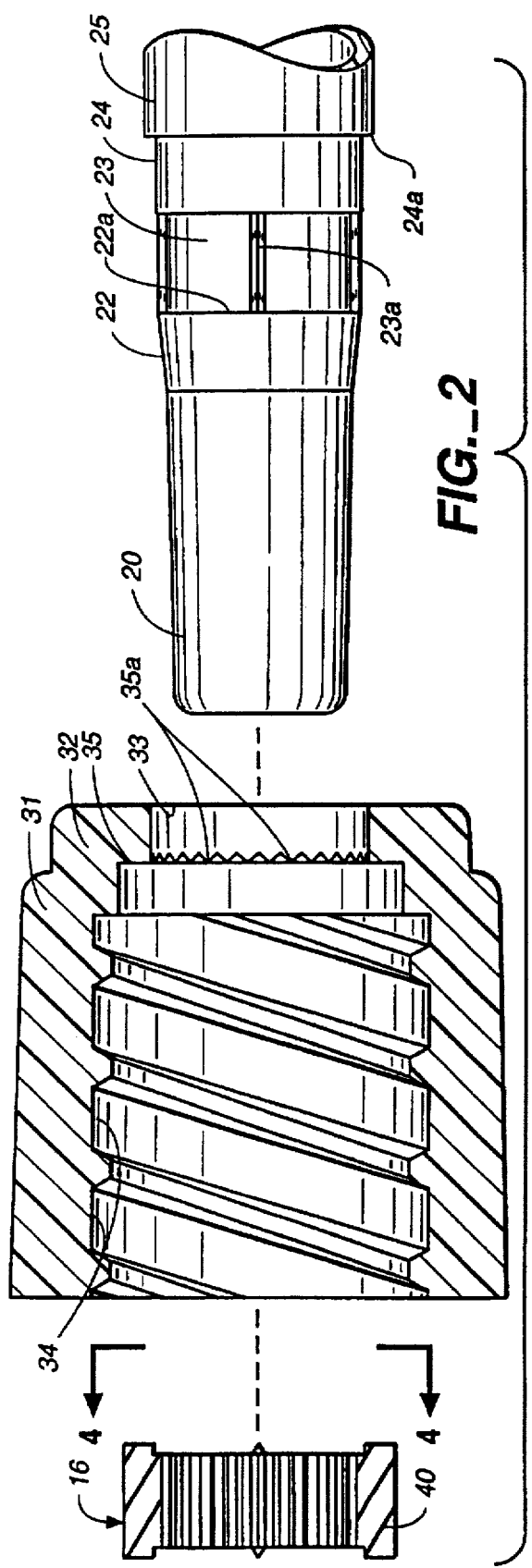
FIG._2
FIG._3
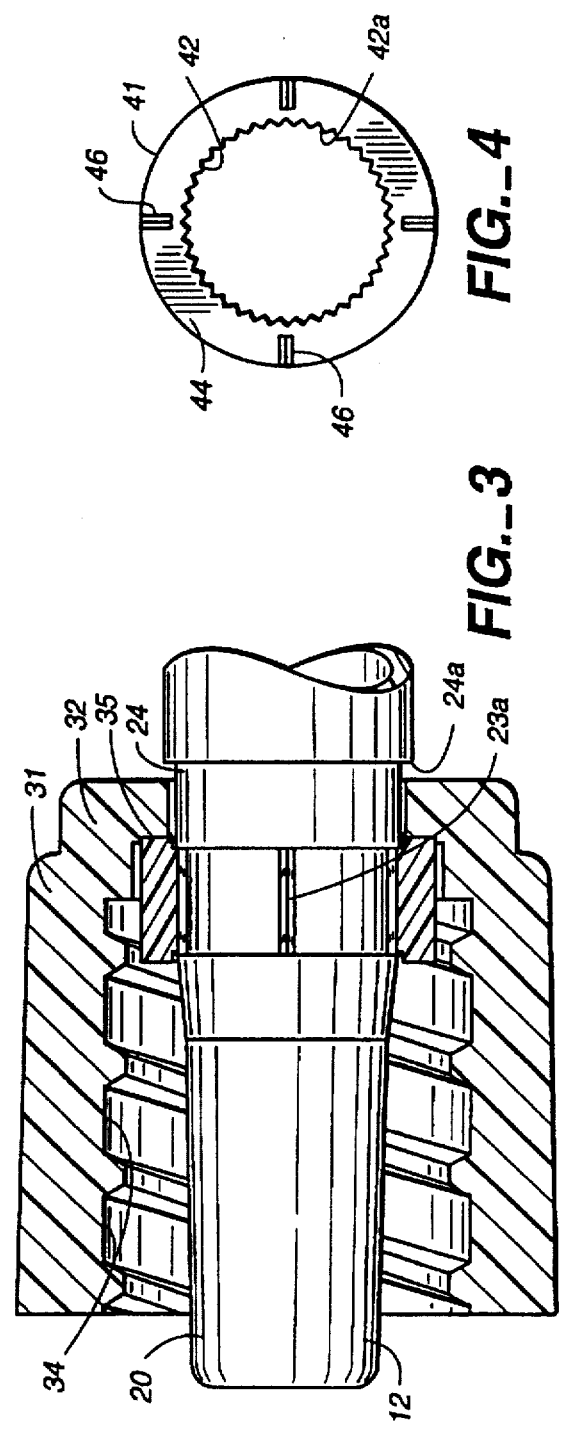
FIG._4

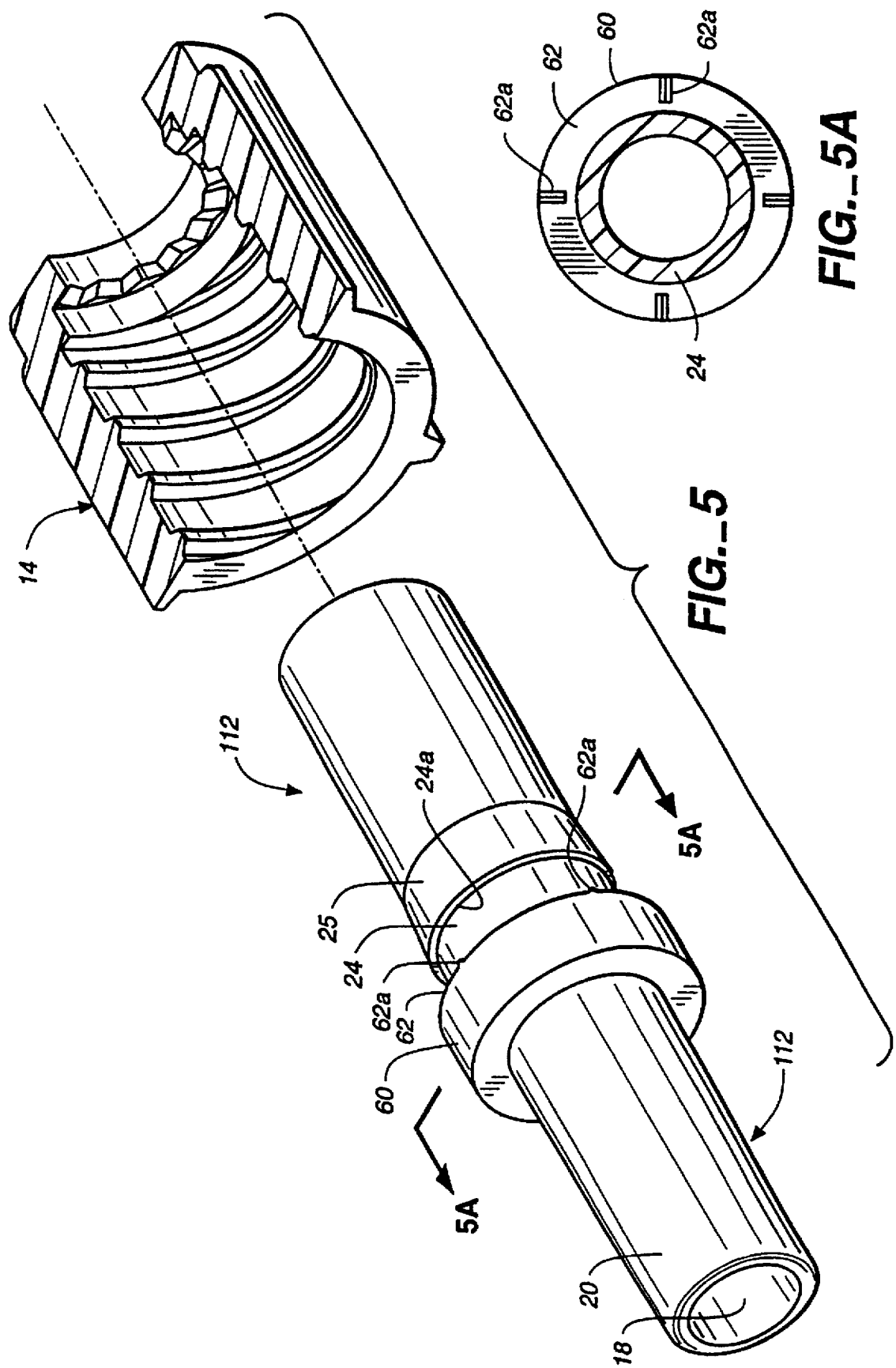

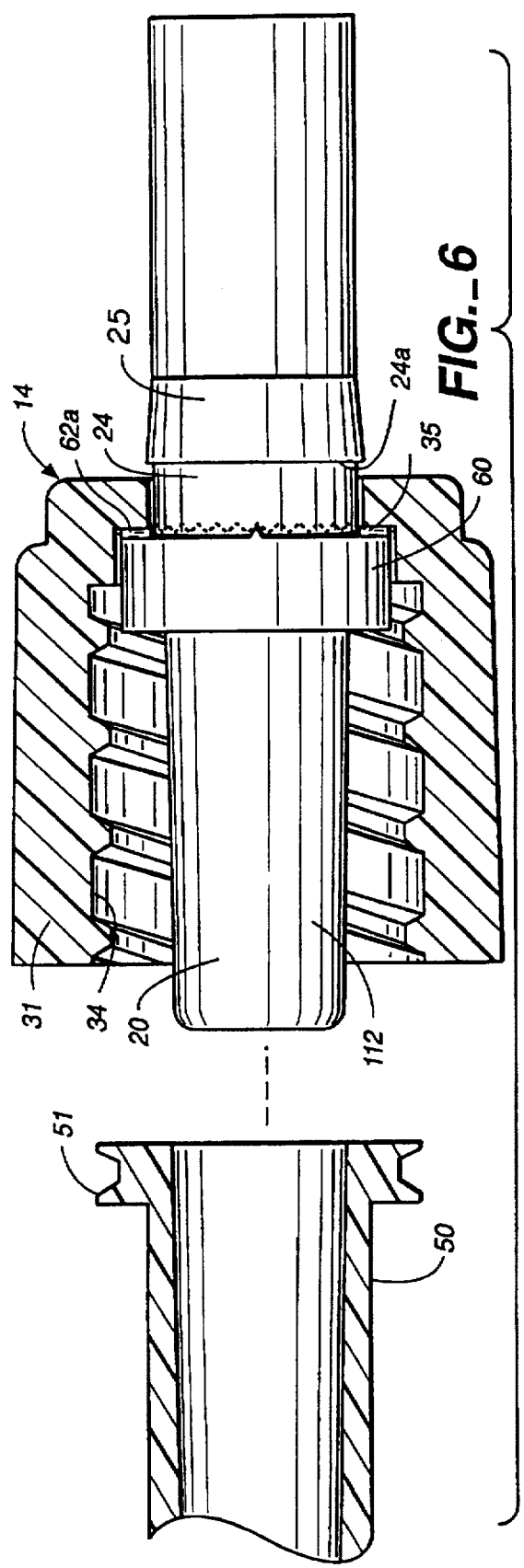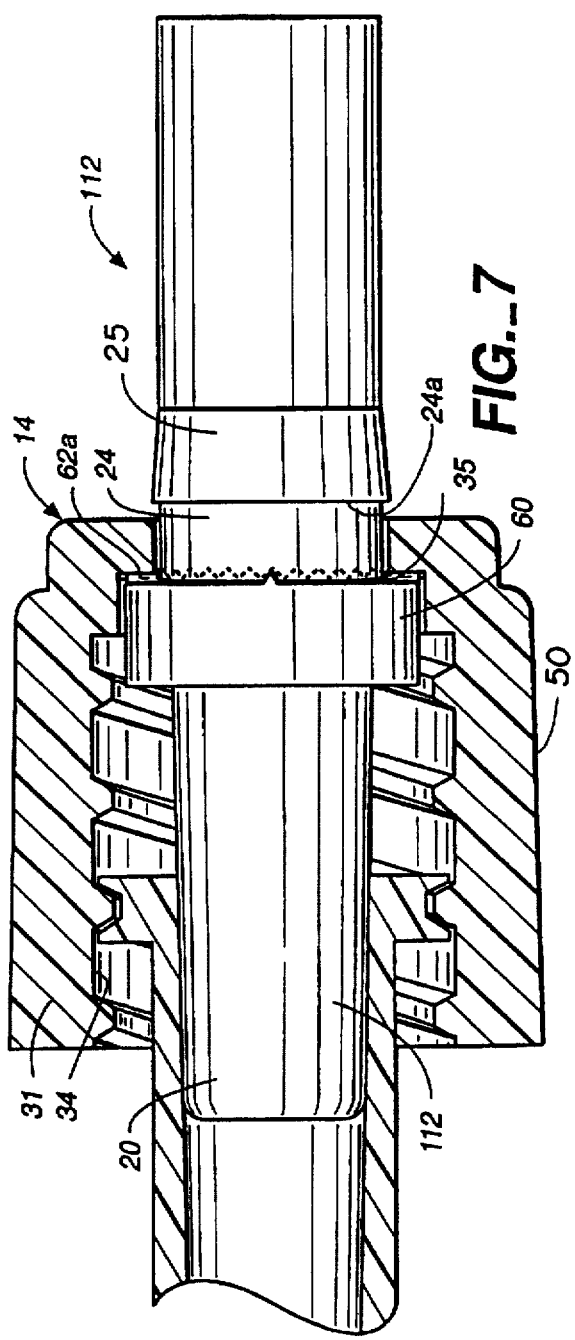

MALE LUER CONNECTOR ASSEMBLY

The present invention pertains to luer connectors generally and in particular to an improved male luer connector assembly devised to provide and maintain a secure fluid/tight fit.

Luer connectors are ubiquitous in the hospital environment. They are used in the critical care unit, the intensive care unit and many hospital-type settings where there is a fluid transfer from a container to a patient. Typically such fluid transfers require a fluid line from a drug or medical fluid container to the patient. Typically that fluid line includes one or more connections between line segments, and most often those connections are provided by luer fittings.

In a typical luer fitting, a male luer connector is inserted into a female luer connector. A lock nut overlying the connection includes an opening associated with the male luer connector which allows the lock nut to descend along the male luer connector to engage a stop associated with male luer connector and then be threaded onto the associated threads of the female luer connector to draw the male luer connector and the female luer connector into fluid-tight engagement.

However, that simple assembly is thwarted by the tendency of most common plastics used in a hospital environment to fatigue or twist loose under prolonged engagement between complementary threaded members. Thus the luer connection can loosen and possibly even disconnect, causing fluid leakage and in some cases a disruption of flow from the fluid container to the patient. Thus, it is appropriate and useful to modify the luer connection so as to assure and maintain a fluid-tight connection for the duration of fluid delivery.

SUMMARY OF THE INVENTION

Accordingly, the present invention modifies and improves the luer connection and provides an improved male luer connector assembly which includes a central elongated male luer connector, such connector tapering from a distal end to a locking collar disposed approximately at the mid-point of the connector.

A recessed section disposed between the first collar and a second collar, the second collar tapered from the recessed section to the main body portion of the luer connector which is generally uniform thereafter to the proximal end of the connector.

The locking collar includes at least a proximal face thereof with locking teeth disposed on said proximal face in spaced relation and a threaded lock nut mountable on the male luer connector, with the end face of the lock nut having an opening therein complementary to the male luer connector so that the lock nut may be slidably mounted on the male luer connector to dispose the end wall of the lock nut on the male luer connector between the locking collar and a second collar of the male luer connector.

The inner peripheral end wall of the lock nut surrounds the male luer connector and carries a plurality of peripheral connecting teeth forming a ratchet at an inner end face of the lock nut.

To enable the connection of said male luer connector assembly to a complementary female threaded luer connector, said male luer connector is inserted into the female threaded luer connector, threads of said threaded lock nut engage the complementary threads of the female luer connector to drive the male luer connector into the female luer connector, while drawing the engaging teeth on the proximal face of the locking collar into engagement with the ratchet on the inner face of the lock nut to ensure and maintain a locking connection between said male luer connector assembly and the female luer connector.

These and other advantages of the improved male luer connector assembly of the present invention will be better understood when the drawings briefly described below are considered with the written specification which follows.

BRIEF DESCRIPTION OF THE DRAWINGS

FIG. 1 is an exploded view of the improved male luer connector assembly of the present invention;

FIG. 2 is an exploded side elevation of the improved male luer connector assembly of FIG. 1 with certain elements of FIG. 2 shown in section to enable a better understanding of the improved male luer connector assembly of the present invention;

FIG. 3 is a view similar to FIG. 2 in which the elements of the improved male luer connectors assembly of FIGS. 1 and FIGS. 2 are shown in an assembled relation;

FIG. 4 is a view taken along the lines 4—4 of FIG. 2;

FIG. 5 is an exploded perspective view similar to the exploded perspective view of FIG. 1 in which an alternative embodiment of the improved male luer connector assembly of the present invention is shown;

FIG. 5A is a view taken along the lines 5A—5A of FIG. 5;

FIG. 6 is a side elevation of the male luer connector assembly of FIG. 5, with the separated elements of the assembly of FIG. 5 shown fully assembled and certain elements also shown in section to enable a better understanding of the present invention, and including a sectioned side elevation of a female luer connector to be joined thereto; and FIG. 7 is a sectional side elevation similar to FIG. 6 in which the improved male luer connector assembly of the present invention and the female luer connector are fully joined.

DETAILED DESCRIPTION OF THE EMBODIMENTS

Referring to FIGS. 1–4 improved male luer connector assembly 10 includes male luer connector 12, lock nut 14 and locking ring 16. The male luer connector 12 is essentially a tube having a fluid passage 18 therethrough. Male luer connector 12 comprises a distal tube portion which is tapered slightly to a tubular section 22 which extends to a locking ring engaging section 23, a lock nut receiving section 24 and a distal section 25 which is generally tubular shaped with little taper.

Lock nut 14 comprises a tubular section 31 and an end wall 32 including an opening 33 therein. At the interior peripheral wall of the tubular section 31 are defined a series of interior threads 34. Disposed adjacent opening 33 on end wall 32 is a ratchet 35 comprising a series of connected annular teeth 35a, which will be described in more detail below.

Locking ring 16 (FIG. 4) completes the assembly. Locking ring 16 (collar) is comprised of an annular ring 40 which has a relatively smooth exterior periphery 41 and a serrated interior periphery 42 comprised of a series of engaging teeth 42a. Disposed within recessed portion 23 of the male luer connector 12 are spaced teeth 23a. In the preferred embodiment the teeth 23a are spaced 90 degrees apart. However, it is possible to provide additional spaced teeth within the recessed section 23 of the male luer connector 12 to provide additional locking connections between the locking ring 16 and the locking ring engaging section 23 as described in more detail below.

The improved male luer connector assembly of the present invention is assembled as shown in FIG. 3. Lock nut 16 moves onto the male luer connector 12 over the distal end thereof to proceed past the tapered section 22, over the locking ring engaging section 23 and the lock nut engaging section 24 to engage shoulder or stop 24a at the proximal end of section 24. Locking ring 16 is then slid onto the male luer connector 12 to move along the male luer connector, past the tapered section 22 and onto the locking ring engaging section 23 where locking teeth 42a of the locking ring engage spaced peripheral teeth 23a of the locking ring engaging section of the male luer connector 12.

Because the locking ring engaging section 23 is recessed with respect to the outer periphery of the male luer connector 12, the locking ring 16 is retained in snap fit engagement within the locking ring engaging section 23 by a peripheral shoulder 22a associated with tapered section 22 and disposed at a proximal end thereof. The peripheral shoulder 22a retains the lock ring 16 on the male luer connector 12.

When the male luer connector 12 is inserted into a female luer connector 50 having corresponding threads 51, the male threads 34 engage the female threads 51 to drive male luer connector into the female luer connector in fluid-tight engagement. The female luer connector will drive the spaced teeth 46 on proximal face 44 of locking ring 16 into the ratchet 35 provided on end wall 32 of the lock nut 14 to secure and maintain the luer connection in fluid-tight engagement.

An alternative embodiment of the improved male luer connector assembly of FIGS. 1–4 is shown in FIGS. 5 and 6. Rather than provide a separate male luer connector 12 and locking ring 16, it may be desirable to integrally mold the locking ring 16 onto the male luer connector as shown in FIG. 5. Such a male luer connector 112 would include the fluid passage 18, the distal body portion 20, lock nut receiving section 24, distal portion end 25 and shoulder or engage stop 24a. Integral locking ring 60 includes spaced peripheral teeth 62a disposed on proximal face 62. Lock nut 14 in FIGS. 5–7 is similar in all respects to the lock nut 14 of the embodiment of FIGS. 1–4.

When the embodiment of. FIG. 5 is assembled as shown in FIG. 7, lock nut 14 overlies locking ring 60 of male luer 112 with spaced peripheral teeth 62a engaging ratchet 35 of lock nut 14 to retain male luer connector 112 and female luer connector 50 in secure and fluid-tight engagement.

While the present invention has been described with respect to the preferred embodiment thereof, those of ordinary skill in the art will understand that further modifications may be made within the scope of the claims that follow. Accordingly, it is not intended that the claims be limited in any way be limited by the disclosure of the preferred embodiments, but that the scope of the invention be defined solely by reference to the claims.

The embodiment of the invention in which an exclusive property or privilege is claimed is described as follows:

We claim:

1. An improved male luer connector assembly comprising:

an elongated male luer connector having a fluid path extending therethrough;

a locking ring having a proximal face, said locking ring being disposed on said male luer connector near the proximal end thereof; and a lock nut rotatably mounted on said male luer connector and overlying said ring, said lock nut having threads along the interior surface thereof for engaging complementary threads on a female luer connector, said ring having a plurality of teeth on said proximal face, and said lock nut including a ratchet on an inner distal face thereof for engaging said plurality of teeth of said ring, whereby to enable the connection of said male luer connector assembly to the complementary threaded female luer connector, said male luer connector is inserted into the threaded female luer connector, the threads of said lock nut engage the complementary threads of the female luer connector and the lock nut is rotated to drive the male luer connector into the female luer connector, while drawing the engaging teeth on the proximal face of the ring into engagement with the ratchet on the inner face of the lock nut, to assure a locking fluid-tight connection between said male luer connector assembly and the female luer connector.

2. The assembly of claim 1 wherein said locking ring is integral with said male luer connector.

3. The assembly of claim 1 wherein said locking ring is removeably mounted to said male luer connector.

4. An improved male luer connector assembly comprising:

(1) an elongated male luer connector having:

a fluid path extending therethrough;

an annular recess disposed near the mid-point of the male luer connector;

a tapered shoulder adjacent the distal end of said recess;

an annular shoulder adjacent the proximal end of said recess; and longitudinal spaced teeth provided on said recess;

(2) a locking ring mountable on the male luer connector having an internal ring of locking teeth at a proximal face, said locking ring mountable on said male luer connector at said annular recess, said locking teeth of the locking ring engageable with the complementary spaced teeth of the recess to prevent rotational movement and said adjacent shoulders engageable with said locking ring to prevent longitudinal movement thereof; and (3) a lock nut rotatably mounted on said male luer connector and overlying said ring, said lock nut having threads on the interior surface thereof for engaging complementary threads on a female luer connector, said ring having teeth spaced on said proximal face, and said lock nut including a ratchet on an inner distal face thereof for engaging said teeth on said proximal face of said ring, whereby to enable the connection of said male luer connector assembly to a complementary threaded female luer connector, said male luer connector is inserted into the threaded female luer connector, the threads of said lock nut engage the complementary threads of the female luer connector, and the lock nut is rotated to drive the male luer connector into the female luer connector, while drawing the engaging teeth on the proximal face of the ring into engagement with the ratchet on the inner face of the lock nut, to assure a locking fluid-tight connection between said male luer connector assembly and the female luer connector.

5. An improved method of connecting a luer connector assembly comprising:

providing an elongated male luer connector having a fluid path extending therethrough;

disposing an annular recess near the mid-point of the male luer connector;

providing a tapered shoulder adjacent the distal end of said recess, and an annular shoulder adjacent the proximal end of said recess;

providing longitudinal spaced teeth on said recess;

mounting a locking ring on the male luer connector at said annular recess, the locking ring having an internal surface of locking teeth and a proximal face;

preventing rotational movement by engagement of the locking teeth of the locking ring with the complementary sapced teeth of the recess;

preventing longitudinal movement by engagement of the locking ring with the adjacent shoulders;

rotatably mounting a lock nut on said male luer connector overlying said ring, said ring having teeth spaced on said proximal face thereof, and said lock nut including threads on the interior surface thereof for engaging complimentary threads on a female luer connector and a ratchet on an inner distal face thereof for engaging said teeth on said proximal face of said ring; and connecting said male luer connector assembly to a complementary threaded female luer connector by inserting said male luer connector into the body of the threaded female luer connector, engaging the threads of said threaded lock nut with the complementary threads of the female luer connector and rotating said locking nut to drive the male luer connector into the female luer connector, while drawing the engaging teeth on the proximal face of the ring into engagement with the ratchet on the inner face of the lock nut, to assure a locking fluid-tight connection between said male luer connector assembly and the female luer connector.

\* \* \* \* \*

UNITED STATES PATENT AND TRADEMARK OFFICE
CERTIFICATE OF CORRECTION

PATENT NO. : 5,702,374
DATED : December 30, 1997
INVENTOR(S) : Johnson

It is certified that error appears in the above-indentified patent and that said Letters Patent is hereby corrected as shown below:

Column 5, line 17, change "sapced" to --spaced--.

Signed and Sealed this

Twenty-sixth Day of May, 1998

Attest:

BRUCE LEHMAN

*Attesting Officer*      *Commissioner of Patents and Trademarks*